(12) United States Patent
Furze et al.

(10) Patent No.: US 7,162,070 B2
(45) Date of Patent: Jan. 9, 2007

(54) USE OF PATTERNED, STRUCTURED LIGHT TO DETECT AND MEASURE SURFACE DEFECTS ON A GOLF BALL

(75) Inventors: Paul A Furze, Tiverton, RI (US); Thomas L Mydlack, Rochester, MA (US)

(73) Assignee: Acushnet Company, Fairhaven, MA (US)

( * ) Notice: Subject to any disclaimer, the term of this patent is extended or adjusted under 35 U.S.C. 154(b) by 685 days.

(21) Appl. No.: 10/456,298

(22) Filed: Jun. 6, 2003

(65) Prior Publication Data

US 2004/0247170 A1    Dec. 9, 2004

(51) Int. Cl.
*G06F 9/00* (2006.01)
(52) U.S. Cl. ...................... 382/141; 382/108
(58) Field of Classification Search ................ 382/141, 382/108; 356/446, 394; 359/156; 250/572
See application file for complete search history.

(56) References Cited

U.S. PATENT DOCUMENTS

| | | | |
|---|---|---|---|
| 5,012,116 A * | 4/1991 | Russell ................ 250/559.46 |
| 5,298,963 A | 3/1994 | Moriya et al. ................ 356/31 |
| 6,031,933 A | 2/2000 | Kumagai ................ 382/141 |
| 6,044,170 A | 3/2000 | Migdal et al. ............. 382/154 |
| 6,122,065 A | 9/2000 | Gauthier ..................... 356/394 |
| 6,327,374 B1 * | 12/2001 | Piironen et al. ............ 382/108 |
| 6,373,607 B1 * | 4/2002 | Rivers et al. ............... 398/152 |
| 6,809,822 B1 * | 10/2004 | Welchman et al. ......... 356/394 |

\* cited by examiner

*Primary Examiner*—Bhavesh M. Mehta
*Assistant Examiner*—Claire Wang
(74) *Attorney, Agent, or Firm*—William B. Lacy

(57) ABSTRACT

A method of inspecting a golf ball, comprising the steps of providing a golf ball; providing a first light source emitting a first color of light; illuminating a first area of the golf ball with the first light source; providing a second light source emitting a second color of light different from the first color of light; illuminating a second area of the golf ball with a second light; providing a first detector comprising a first filter for transmitting the first color of light and filtering out the second color of light; providing a second detector comprising a second filter for transmitting the second color of light and filtering out the first color of light; rotating the ball about an axis; and detecting a shadow resulting from illumination by the first or second light sources.

14 Claims, 2 Drawing Sheets

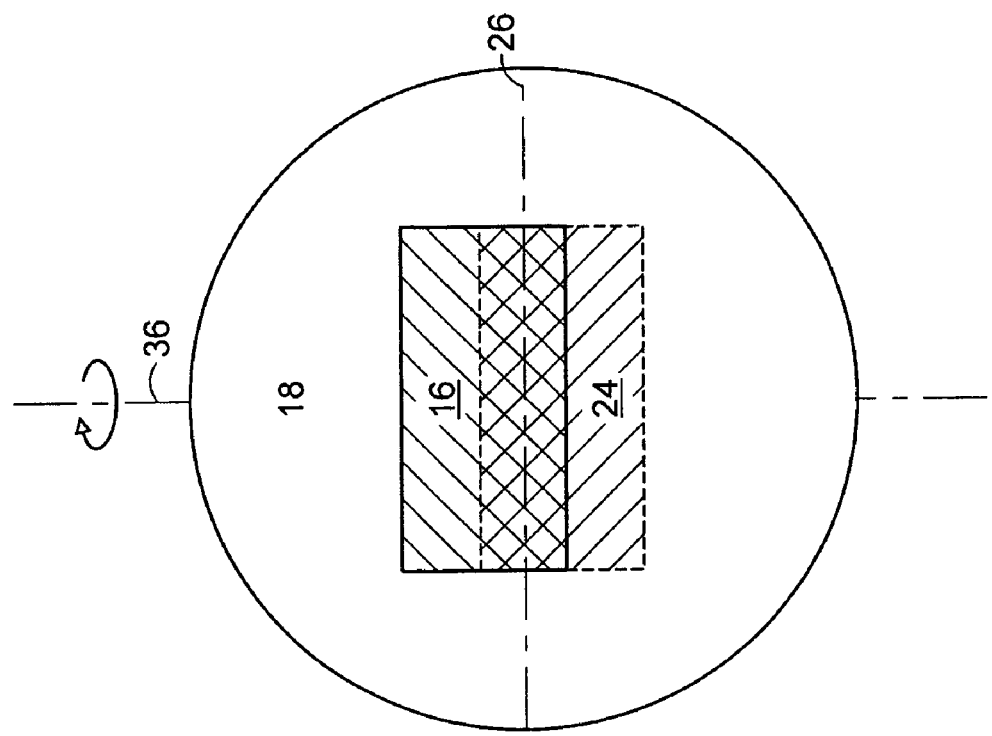
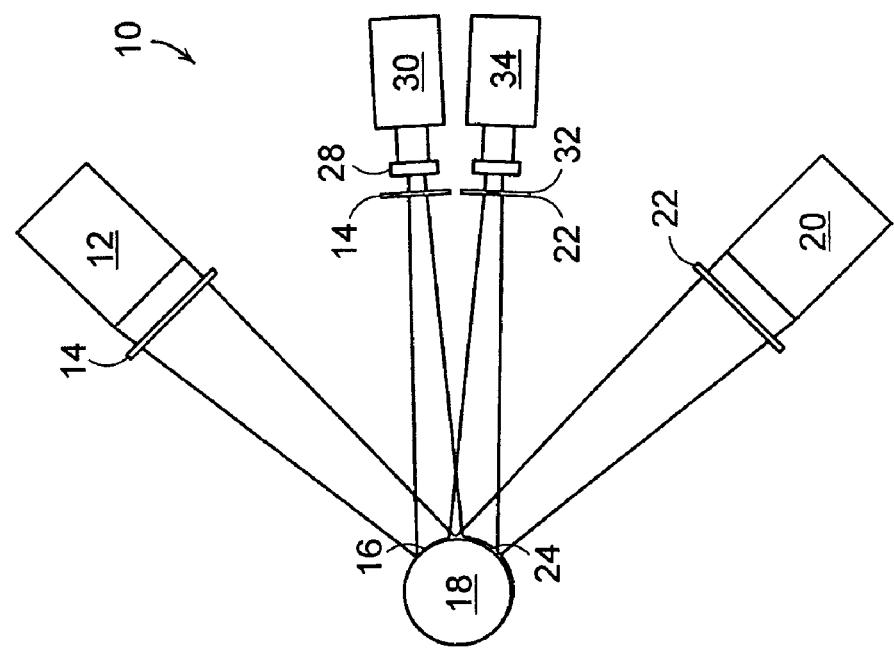

USE OF PATTERNED, STRUCTURED LIGHT TO DETECT AND MEASURE SURFACE DEFECTS ON A GOLF BALL

BACKGROUND OF THE INVENTION

In the manufacture of golf balls defects, such as flow lines, excess cover material, weld marks, protrusions, gate marks, depressions, buffing lines, paint blots, stuck molding flash, blisters, and other foreign matter (i.e., dirt, particulate, etc.), can form on the surface of the golf balls for a variety of reasons. Golf balls having such defects can be aesthetically displeasing and may exhibit a loss in aerodynamic performance. As such, it is common practice within the golf ball industry to inspect, in some manner, the surface of the golf balls for defects prior to painting (if necessary), packaging, and shipping.

Conventionally, golf balls are inspected manually. But given the excessive number of golf balls produced in a year (e.g. Titleist®, the number one ball in golf, produces over 276 million golf balls per year), however, manual inspection of every golf ball is physically and logistically impossible and, additionally, is very subjective. Manufacturers have, therefore, attempted to automate the inspection process and incorporate the inspection somewhere in the golf ball manufacturing sequence. Automated golf ball surface inspection is difficult, however, because of a golf ball's unique surface topography—curved and dimpled.

A substitute for visual inspection that is commonly employed to automatically inspect the outer surface of a golf ball typically includes taking an optical image of the ball and processing the image by comparing it to a reference standard. When the object to be inspected is dimpled, such as a golf ball, the difficulties in detecting defects on the surface are greatly increased. Because dimples are distributed on a spherical surface, they can appear in the image as artifacts, such as ellipsoids having indefinite major and minor axes shadows. It is, therefore, important for a detection system to be able to detect the difference between a dimple and a defect on the curved, dimpled surface.

U.S. Pat. No. 6,031,933 discloses one such method for inspecting the outer surface of a golf ball. In the '933 patent, the outer surface of a golf ball is inspected for defects by illuminating the golf ball with a single light source, rotating the golf ball at a constant speed in one direction, and taking a series of line images of the ball surface with a line sensor camera along a line perpendicular to the rotational direction of the ball. The camera then delivers the one-dimensional line data to a computer that assembles it into a two-dimensional image, converts a brightness change in the two-dimensional image in the rotational direction of the ball into a variation per preset unit, and subjects the resulting variation data to binary processing on the basis of a threshold set between the variation associated with the dimple and the variation associated with any defects, thereby detecting whether or not defects are present. Effectively, a light threshold, based on the dynamic range of the line data, is determined—light levels darker than the threshold value are deemed a defect and light levels above the threshold value are deemed not a defect (i.e., a shadow or dark area, that does not match the intensity profile of a dimple, represents a defect).

The '933 patent, however, is limited in the 'area' of the surface that can be inspected. Because the surface of a golf ball is curved and light does not bend, as one moves away from the equator (or center of the illumination) of the ball, the golf ball surface itself begins to appear as a shadow in a collected line (or two-dimensional) image, limiting the effectiveness of the imaging method. Because of their varying and non-discriminating nature, surface defects, unfortunately, are not limited to specific areas of a golf ball. The method of the present invention provides a novel way to address this issue by adding a second illumination source having a different wavelength (or range of wavelengths) than the first illumination source, in combination with an array of pass filters and two-dimensional area imaging (versus line imaging).

SUMMARY OF THE INVENTION

The present invention is directed to a method of inspecting a golf ball, comprising the steps of providing a golf ball; providing a first light source emitting a first color of light; illuminating a first area of the golf ball with the first light source; providing a second light source emitting a second color of light different from the first color of light; illuminating a second area of the golf ball with a second light; providing a first detector comprising a first filter for transmitting the first color of light and filtering out the second color of light; providing a second detector comprising a second filter for transmitting the second color of light and filtering out the first color of light; rotating the ball about an axis; and detecting a shadow resulting from illumination by the first or second light sources.

The second area preferably has a different geometric center than the first area, but is preferably parallel and overlapping. The area of the golf ball to be imaged is preferably on either side of its equator (or parting line) which would be disposed between the first and second imaging areas.

The method further may include the step of capturing an image of each of the first and second areas with the first and second detectors. The images may be compared or analyzed individually for defects. It is preferred that the first light source have a first wavelength range and the second light source has a second wavelength range that is substantially different from the first. In a preferred embodiment, the first wavelength range is between about 480 nm and about 530 nm and the second wavelength range is between about 600 nm and about 680 mm.

In one embodiment, a first polarizer is located between at least one of the light sources and the golf ball and a second polarizer is located between the golf ball and at least one of the detectors, the second polarizer being oriented orthogonal to the first.

The first or second detectors are preferably one of a charge-coupled device, a photomultiplier tube, an avalanche photodiode, or a video camera. The first or second filters typically include a high-pass filter, a low-pass filter, a notch filter, or a holographic notch filter. The first or second light sources generally are one of a light-emitting diode, a laser, a colored lamp, or an arc lamp.

The axis of rotation of the golf ball for imaging should be perpendicular to a plane defined by the equator or parting line of the ball. The light sources and/or detectors can be oriented in any reference frame relative to the defined plane. In a preferred embodiment, the first and second areas are parallel and not overlapping.

The present invention is also directed to a method of inspecting a golf ball, comprising the steps of translating a golf ball for inspection, the golf ball having an equator; providing a first light source emitting a first color of light having a first wavelength range; illuminating a first area of the golf ball with the first light source; providing a first polarizer disposed between the first light source and the golf ball; providing a second light source emitting a second color of light having a second wavelength range substantially different from the first; illuminating a second area of the golf ball with a second light, the second area being parallel to and overlapping the first; providing a second polarizer disposed between the second light source and the golf ball; providing a first detector comprising a first filter for transmitting the first wavelength range and filtering out the second wavelength range; providing a second detector comprising a second filter for transmitting the second wavelength range and filtering out the first wavelength range; rotating the ball about an axis perpendicular to a plane defined by the equator; capturing an image of the first and second areas with the first and second detectors; and analyzing the image for a shadow indicative of surface defects. In one embodiment, the method further includes the step of providing at least one third polarizer disposed between the golf ball and the detectors, the third polarizer being orthogonal to the first and second polarizers.

The present invention is further directed to a method of inspecting a curved surface, comprising the steps of providing the curved surface for inspection; providing a first light source emitting a first color of light having a first wavelength range; illuminating a first area of the curved surface with the first light source; providing a second light source emitting a second color of light having a second wavelength range substantially different from the first; illuminating a second area of the curved surface with a second light, the second area being parallel to the first; providing a first detector comprising a first filter for transmitting the first wavelength range and filtering out the second wavelength range; providing a second detector comprising a second filter for transmitting the second wavelength range and filtering out the first wavelength range; rotating the curved surface; capturing an image of the first and second areas with the first and second detectors; and analyzing the images for a shadow indicative of surface defects. In one embodiment, the curved surface includes a golf ball center, golf ball core, golf ball layer, or a golf ball.

BRIEF DESCRIPTION OF THE DRAWINGS

FIG. 2 is a diagram of one embodiment of the inspection system; and

FIG. 3 is a view of the overlapped regions inspected by the inspection system.

DETAILED DESCRIPTION OF THE INVENTION

Figure 1:
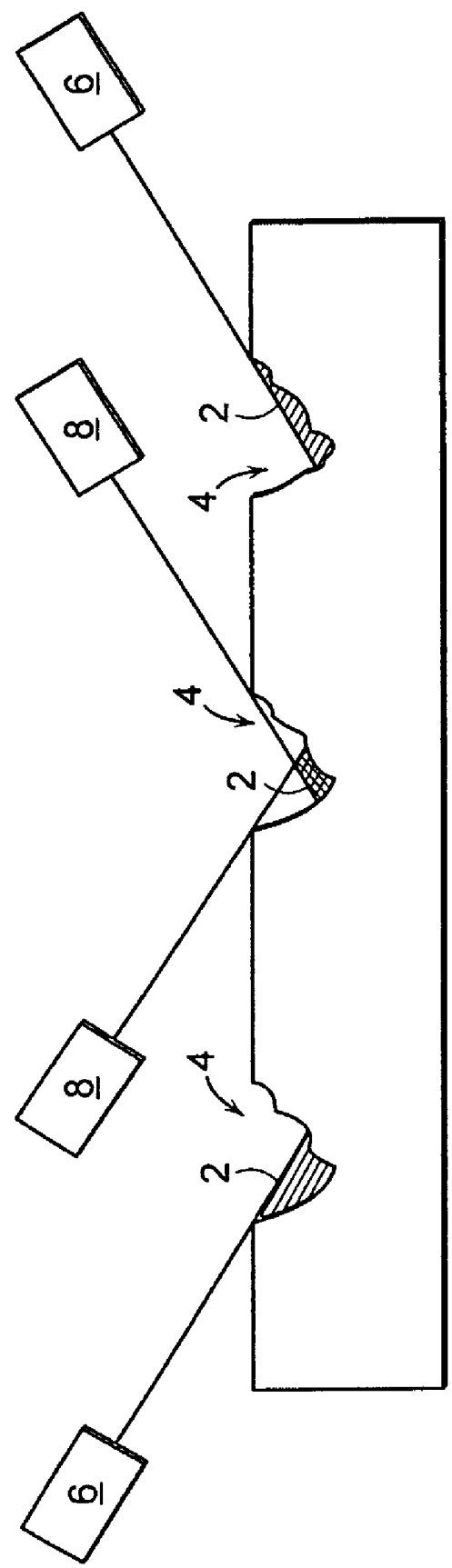
FIG. 1 is a cross section of a golf ball surface showing the effect of shadow cancellation.

The automated inspection system of the present invention is suitable for use on the surface of any golf ball component, such as centers, cores, core layers, intermediate layers, and cover layers or coatings. Preferably, the inspection system is used to inspect the outer surface of cores or covers.

The inspection system of the present invention typically includes at least one golf ball, a translation and rotation system, 2 light sources, 2 detectors, and 2 filters. Generally, a golf ball to be inspected is translated into a position for inspection. Although not shown, the inspection system is attached to a computer (or self-contained vision system) and for subsequent analysis and image processing. The computer and monitor may be combined into a single element or be separate elements. The computer has several algorithms and programs used by the system to make the determinations discussed below.

A first light source illuminates the golf ball at a first wavelength and a second light source illuminates the golf ball at a second wavelength, the second wavelength being different from the first. It is preferred that at least 2 light sources are used so that the region of inspection is maximized. It is well understood that a curved surface provides difficult challenges to overcome, in particular when light, varying angles, and shadows therefrom are involved.

Referring to FIG. 1, shadows 2 caused by surface defects 4 are easily 'seen' when illuminated with a single light source 6. A problem arises, however, when two light sources 8 are employed. In FIG. 1, the center defect clearly shows that the two light sources impinging on the defects 4 result in cancellation of the shadows 2. As such, these defects 4 would not be detected if the detection system were to rely solely on shadows 2 to indicate such anomalies.

Referring to FIGS. 2 and 3, the inspection system of the present invention recognizes and overcomes this problem by requiring that the light sources have different wavelengths and further including a filter (i.e., color, high-pass, low-pass, notch, holographic, etc.) between the illuminated golf ball surface and each detector. This configuration results in a system in which each of the detectors are specific to (because of filtering) the wavelength (or wavelength range) of each light source and that 'passed' by the filter. FIG. 2 shows a preferred embodiment of the inspection system 10 of the present invention and includes a first light source 12 and a polarizer 14 for illuminating a first area 16 of a golf ball 18. A second light source 20 and polarizer 22 illuminate a second area 24 of golf ball 18. The polarizers, 14 and 22, may or may not be present but can help eliminate specular glare, especially when illuminating a reflective surface. Further, the polarizers, 14 and 22, are preferably present both between the light sources, 12 and 20, and the golf ball 18, as well as between the detectors, 30 and 34, and the golf ball 18. Most preferably, the polarizers, 14 and 22, are oriented orthogonal to one another.

The first and second areas, 16 and 24, may or may not overlap. Preferably the first and second areas, 16 and 24, overlap, more preferably about the equator 26 or parting line of golf ball 18. Referring to FIG. 2, the image resulting from illumination by the first light source 12 passes through first filter 28 and is captured by first detector 30. The image resulting from illumination by the second light source 20 passes through a second filter 32 and is captured by second detector 34.

The first and second light sources, 12 and 20, can be any light source, but are preferably a light-emitting-diode ("LED"), a colored lamp, or a laser. Additionally, a multi-wavelength light source, such as an arc lamp, may be used in combination with a filter that passes only a single (or narrow band) wavelength of light prior to striking the golf ball surface. The first and second filters, 28 and 32, can be any filter that passes the wavelength of light of the first light source 12 but does not pass the wavelength of light from the second light source 20. Preferably, the filters are a high-pass filter (allows long wavelengths to pass but blocks short wavelengths); a low-pass filter (allows short wavelengths to pass but blocks long wavelengths); a notch filter (allows only a narrow band of wavelengths to pass, i.e., a green notch filter might allow 500–525 nm light to pass while blocking all other wavelengths); or a holographic notch filter (allows only a single wavelength of light to pass; typically used with laser illumination).

For example, consider a first light source to be a green light, having a wavelength of about 500 nm, and a second light source to be a red light, having a wavelength of about 650 nm. In this case, the detector for the first light source would have a filter that passed only green light (but no red light) and the detector for the second light source would have a filter that passed only red light (but no green light). This combination would eliminate the shadow-canceling problem and allow twice the area to be probed for defects than were a single camera used.

While any light-sensitive detector, capable of imaging an area, is suitable for the inspection system 10 of the present invention, preferred detectors include, but are not limited to, charge-coupled device-based detectors, photomultiplier tubes, avalanche photodiodes, and digital video cameras. First and second detectors, 30 and 34, are most preferably charge-coupled device ("CCD") based, such as the ELECTRIM® EDC-1000U computer camera from Electrim Corporation in Princeton, N.J. CCD's are two-dimensional silicon-metal oxide arrays that are nearly ideal for a variety of imaging needs, especially those requiring detection at low light levels. CCD detectors have a number of characteristic advantages over other multi-channel detectors, such as photomultiplier tubes, including high quantum efficiency in the visible spectrum, excellent charge-transfer efficiency, low read noise and dark current, wide dynamic range, and image plane stability. Utilization of the CCD as a detector is based on collecting and storing photon-induced charge on a continuous silicon substrate (array) divided into individual elements (pixels) by a series of electrodes which are used to manipulate the charge. Exposure of this two-dimensional imaging area leads to charge accumulation that is localized by potential wells established by electrodes on the detector surface. This two-dimensional "image" can then be transferred to a serial register by a series of potentials applied to the electrodes and on to a monitor for viewing by the user.

The detectors preferably each have a line-of-sight directed to and focused on a predetermined focal length. The focal length of the detectors can be any focal length but is preferably larger than required to image a single golf ball. The detectors are most preferably directed and focused on a predetermined field-of-view in which the golf ball moves into and out of, during which it is imaged.

The light from the first and second light sources, 12 and 20, is preferably directly illuminating, but may also be directed by mirrors, lenses, prisms, fiber optics, or a combination of these. It is also envisioned that UV or IR irradiation could be employed or that a single wavelength light source, in combination with a strobe or alternating time delay might be used in the inspection system.

The golf ball 18 may be delivered in any manner into the field of view of the inspection system 10. Proper orientation of the ball is important so that the maximum area of the surface can be imaged. Preferably, the golf ball is oriented so that the field of view of the 2 detectors, 30 and 34, is overlapping, just above and below the equator 26 of the ball 18. This can be seen clearly in FIG. 3. The golf ball 18 is then preferably rotated about an axis 36 perpendicular to the plane defined by the equator 26 so that the entire circumference of the golf ball 18 can be inspected. Preferably the golf ball is rotated continuously but in an alternative embodiment, the golf ball 18 is rotated incrementally.

The inspection system 10 can be oriented at any angle relative to the equator 26 and golf ball 18, as long as the light illuminates the proper areas of the surface and the detectors, 30 and 34, can collect the area-scan image. In two alternative embodiments, the golf ball 18 is rotated on more than 1 axis or the combination of the light sources, filters, and detectors are rotated or translated.

In an alternative embodiment of the present invention, structured light, in the form of a Moiré pattern (or, alternatively, a grid or line scan pattern), is projected onto the surface of a golf ball. Moiré fringes are an interference pattern that is formed when two similar grids overlap each other. The result is a series of fringe patterns that change shape when as the grids are translated. While typically used to measure the profiles of flat surfaces, in this alternative embodiment it is desired that the lines of the Moiré pattern, when projected onto a curved surface, can effectively serve as "topographical" lines to map the golf ball surface and any defects thereon. Upon detection and analysis, any variations in the Moiré "topographical" pattern would indicate variations or imperfections in the golf ball surface—defects.

An additional Moiré pattern embodiment involves projecting the Moiré pattern onto the curved golf ball surface at a predetermined angle to the viewing axis. If part of the golf ball surface is raised or indented (i.e., a surface defect exists), the Moiré pattern will shift toward or away from the light source.

Alternatively, a single line could be projected onto the golf ball surface at a predetermined angle relative to the viewing axis. Any raised or indented areas (surface defects) would again shift the line toward or away from the light source. In this embodiment, the golf ball (or surface being analyzed) could be iteratively shifted and/or rotated to allow the entire surface to be mapped. In a preferred embodiment, the line projected on the curved surface is pre-curved so that it appears on the curved golf ball surface as a straight line. It is well understood that a straight line projected onto a curved surface results in an arc-shaped line—processing or analyzing the area around an arc is time consuming. Adjusting the projection as above will allow simpler and faster analysis of the golf ball surface. It is also envisioned that this method would work using a single point in place of a line.

The term "about", as used herein in connection with one or more numbers or numerical ranges, should be understood to refer to all such numbers, including all numbers in a range.

The invention described and claimed herein is not to be limited in scope by the specific embodiments herein disclosed, since these embodiments are intended solely as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method of inspecting a golf ball, comprising the steps of:

providing a golf ball;
   providing a first light source emitting a first color of light;
   illuminating a first area of the golf ball with the first light source;
   providing a second light source emitting a second color of light different from the first color of light;
   illuminating a second area of the golf ball with a second light;
   providing a first detector comprising a first filter for transmitting the first color of light and filtering out the second color of light;

providing a second detector comprising a second filter for transmitting the second color of light and filtering out the first color of light;

providing a first polarizer located between at least one of the light sources and the golf ball and a second polarizer located between the golf ball and at least one of the detectors, the second polarizer being oriented orthogonal to the first:

rotating the ball about an axis; and detecting a shadow resulting from illumination by the first or second light sources.

2. The method of claim 1, wherein the second area has a different geometric center than the first area.

3. The method of claim 1, wherein the golf ball has an equator or a parting line disposed between the first and second areas.

4. The method of claim 1, further comprising the step of capturing an image of the first and second areas with the first and second detectors.

5. The method of claim 1, wherein the first light source has a first wavelength range and the second light source has a second wavelength range different from the first.

6. The method of claim 5, wherein the first wavelength range is between about 480 nm and about 530 nm and the second wavelength range is between about 600 nm and about 680 nm.

7. The method of claim 1, wherein the first or second detectors comprise a charge-coupled device, a photomultiplier tube, an avalanche photodiode, or a video camera.

8. The method of claim 1, wherein the first or second filters comprise a high-pass filter, a low-pass filter, a notch filter, or a holographic notch filter.

9. The method of claim 1, wherein the first or second light sources comprise a light-emitting diode, a laser, a colored lamp, or an arc lamp.

10. The method of claim 1, wherein the axis of rotation is perpendicular to a plane defined by the equator or parting line.

11. The method of claim 1, wherein the first and second areas are parallel and not overlapping.

12. A method of inspecting a golf ball, comprising the steps of:

translating a golf ball for inspection, the golf ball having an equator;

providing a first light source emitting a first color of light having a first wavelength range;

illuminating a first area of the golf ball with the first light source;

providing a first polarizer disposed between the first light source and the golf ball;

providing a second light source emitting a second color of light having a second wavelength range substantially different from the first;

illuminating a second area of the golf ball with a second light, the second area being parallel to and overlapping the first;

providing a second polarizer disposed between the second light source and the golf ball;

providing a first detector comprising a first filter for transmitting the first wavelength range and filtering out the second wavelength range;

providing a second detector comprising a second filter for transmitting the second wavelength range and filtering out the first wavelength range;

rotating the ball about an axis perpendicular to a plane defined by the equator;

capturing an image of the first and second areas with the first and second detectors; and analyzing the image for a shadow resulting from illumination by the first or second light sources, the shadow being indicative of surface defects.

13. The method of claim 12, further comprising the step of providing at least ones third polarizer disposed between the golf ball and the detectors, the third polarizer being orthogonal to the first and second polarizers.

14. A method of inspecting a golf ball, comprising the steps of:

providing a dimpled curved surface for inspection;

providing a first light source emitting a first color of light having a first wavelength range;

illuminating a first area of the curved surface with the first light source;

providing a second light source emitting a second color of light having a second wavelength range substantially different from the first;

illuminating a second area of the curved surface with a second light, the second area being parallel to the first;

providing a first detector comprising a first filter for transmitting the first wavelength range and filtering out the second wavelength range;

providing a second detector comprising a second filter for transmitting the second wavelength range and filtering out the first wavelength range;

providing a first polarizer located between at least one of the light sources and the golf ball and a second polarizer located between the golf ball and at least one of the detectors, the second polarizer being oriented orthogonal to the first;

rotating the curved surface;

capturing an image of the first and second areas with the first and second detectors; and analyzing the images for a shadow resulting from illumination by the first or second light sources, the shadow being indicative of surface defects.

* * * * *